US00PP17638P2

(12) United States Plant Patent
Smith

(10) Patent No.: US PP17,638 P2
(45) Date of Patent: Apr. 24, 2007

(54) ***HIBISCUS* PLANT NAMED 'CARAFE YOBORDEAUX'**

(50) Latin Name: *Hibiscus moscheutos*
Varietal Denomination: Carafe Yobordeaux

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 68 days.

(21) Appl. No.: 11/178,272

(22) Filed: Jul. 8, 2005

(51) Int. Cl.
*A01H 5/00* (2006.01)

(52) U.S. Cl. ..... Plt./257
(58) Field of Classification Search ..... Plt./257
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'Carafe Yobordeaux', characterized by its upright and outwardly spreading plant habit; freely branching and moderately vigorous growth habit; early flowering habit; large red purple-colored flowers; and excellent garden performance.

2 Drawing Sheets

Botanical designation: *Hibiscus moscheutos.*
Cultivar denomination: 'Carafe Yobordeaux'.

BACKGROUND OF THE INVENTION

The present invention relates to a new and distinct cultivar of *Hibiscus,* botanically known as *Hibiscus moscheutos,* and hereinafter referred to by the name 'Carafe Yobordeaux'.

The new *Hibiscus* is a product of a planned breeding program conducted by the Inventor in Salinas, Calif. and Alva, Fla. The objective of the breeding program is to create new freely-branching and *Hibiscus* cultivars with a compact plant habit and attractive flower coloration.

The new *Hibiscus* originated from a cross-pollination made by the Inventor in Salinas, Calif. during the summer of 2000, of the *Hibiscus moscheutos* cultivar Disco Belle Red, not patented, as the female, or seed, parent with the *Hibiscus moscheutos* cultivar Blue River II, not patented, as the male, or pollen, parent. The cultivar Carafe Yobordeaux was discovered and selected by the Inventor as a flowering plant within the progeny of the stated cross-pollination in a controlled environment in Alva, Fla. on May 29, 2001.

Asexual reproduction of the new *Hibiscus* by vegetative terminal cuttings in a controlled environment in Alva, Fla. since June, 2001, has shown that the unique features of this new *Hibiscus* are stable and reproduced true to type in successive generations.

SUMMARY OF THE INVENTION

The cultivar Carafe Yobordeaux has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Carafe Yobordeaux'. These characteristics in combination distinguish 'Carafe Yobordeaux' as a new and distinct cultivar:

1. Upright and outwardly spreading plant habit.
2. Freely branching and moderately vigorous growth habit.

3. Early flowering habit.
4. Large red purple-colored flowers.
5. Excellent garden performance.

Plants of the new *Hibiscus* can be compared to plants of the female parent, the cultivar Disco Belle Red. Plants of the new *Hibiscus* differ from plants of the unnamed whole plant mutation of the cultivar Disco Belle Red in the following characteristics:

1. Plants of the new *Hibiscus* are taller and fuller than plants of the cultivar Disco Belle Red.
2. Plants of the new *Hibiscus* flower about four days later than plants of the cultivar Disco Belle Red.
3. Plants of the new *Hibiscus* have larger flowers than plants of the cultivar Disco Belle Red.

Plants of the new *Hibiscus* can be compared to plants of the male parent, the cultivar Blue River II. Plants of the new *Hibiscus* differ from plants of the cultivar Blue River II in the following characteristics:

1. Plants of the new *Hibiscus* are shorter and fuller than plants of the cultivar Blue River II.
2. Plants of the new *Hibiscus* flower about two days earlier than plants of the cultivar Blue River II.
3. Plants of the new *Hibiscus* and the cultivar Blue River II differ in flower coloration as plants of the cultivar Blue River II have white-colored flowers.

Plants of the new *Hibiscus* can be compared to plants of the *Hibiscus* cultivar Lady Baltimore, not patented. In side-by-side comparisons conducted in Alva, Fla., plants of the new *Hibiscus* differed from plants of the cultivar Lady Baltimore in the following characteristics:

1. Plants of the new *Hibiscus* were shorter, fuller and stronger than plants of the cultivar Lady Baltimore.
2. Plants of the new *Hibiscus* and the cultivar Lady Baltimore differed in leaf shape.
3. Plants of the new *Hibiscus* flowered about two days later than plants of the cultivar Lady Baltimore.
4. Plants of the new *Hibiscus* had lighter red purple-colored flowers than plants of the cultivar Lady Baltimore.

Plants of the new *Hibiscus* can also be compared to plants of the *Hibiscus* cultivar Luna Red, not patented. In side-by-side comparisons conducted in Alva, Fla., plants of the new *Hibiscus* differed from plants of the cultivar Luna Red in the following characteristics:

1. Plants of the new *Hibiscus* were taller than plants of the cultivar Luna Red.
2. Plants of the new *Hibiscus* flowered about four days later than plants of the cultivar Luna Red.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of a typical flowering plant of 'Carafe Yobordeaux' grown in an outdoor nursery in Alva, Fla. for about six months.

The photograph on the second sheet comprises a close-up view of a typical flower of 'Carafe Yobordeaux'.

DETAILED BOTANICAL DESCRIPTION

The following observations, measurements and values describe plants grown in Alva, Fla. in one-gallon containers in a polypropylene-covered shadehouse during the summer and under conditions which closely approximate commercial production. During the production of the plants, day temperatures ranged from 29° C. to 32° C. and night temperatures ranged from 21° C. to 24° C. Plants were pinched about five weeks after planting. The description was taken about two months after the pinch. In the description, color references are made to The Royal Hoticultural Society Colour Chart, 1995 Edition, except where general terms of ordinary dictionary significance are used.

Botanical classification: *Hibiscus moscheutos* cultivar Carafe Yobordeaux.

Parentage:

*Female or seed parent.*—*Hibiscus moscheutos* cultivar Disco Belle Red, not patented.

*Male or pollen parent.*—*Hibiscus moscheutos* cultivar Blue River II, not patented.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick, fibrous; white in color.

*Rooting habit.*—Freely branching.

Plant description:

*Plant form and growth habit.*—Perennial shrub; upright and outwardly spreading plant habit. Moderately vigorous growth habit.

*Branching habit.*—Freely branching, lateral branches potentially forming at every node.

*Plant height.*—About 31 cm.

*Plant diameter* (*area of spread*).—About 36 cm.

*Lateral branch description.*—Length: About 22 cm. Diameter: About 9 mm. Internode length: About 1.9 cm. Texture: Smooth, glabrous. Color: 144A to 146A.

*Foliage description.*—Arrangement: Alternate, simple. Length: About 9.1 cm. Width: About 7 cm. Shape: Cordate to ovate. Apex: Acute; narrowly tapering. Base: Cordate. Margin: Crenate; slightly undulate. Texture, upper and lower surfaces: Smooth, glabrous. Venation pattern: Palmate. Color: Developing foliage, upper surface: Slightly darker green than 147A. Developing foliage, lower surface: Close to 191A. Fully expanded foliage, upper surface: Close to than 147A. Fully expanded foliage, lower surface: Close to 191A. Venation, upper surface: Towards the margins, 147A; towards the base, close to 187A. Venation, lower surface: 191A to 146A. Petiole: Length: About 4.4 cm. Diameter: About 4 mm. Texture, upper and lower surfaces: Smooth, glabrous. Color, upper surface: Close to 146A overlain with 187A. Color, lower surface: Close to 146A.

Flower description:

*Flower arrangement.*—Flowers develop at axillary leaf axils; typically one or two flowers per axil. Flowers face upright to outward.

*Flower appearance.*—Rotate red purple-colored flowers. Flowers are open for about two days. Flowers persistent.

*Natural flowering season.*—Usually spring and summer or during periods of warm weather.

*Flower diameter.*—About 11.5 cm.

*Flower length* (*height*).—About 3.5 cm.

*Flower bud.*—Length: About 2.2 cm. Diameter: About 1.7 cm. Shape: Ovoid. Color: Close to 146C.

*Petals.*—Quantity/arrangement: Corolla consists of five petals; petals imbricate. Length: About 6.3 cm. Width: About 5.5 cm. Shape: Roughly spatulate to orbicular. Apex: Rounded; undulate. Base: Attenuate. Margin: Entire to slightly crenate; undulate. Texture, upper and lower surfaces: Smooth, glabrous; satiny; rugose. Color: When opening and fully opened, upper surface: Close to 59A to 59B. When opening and fully opened, lower surface: Close to 59B.

*Sepals.*—Quantity/arrangement: Five sepals fused into a tubular calyx. Length: About 2.3 cm. Width: About 2 cm. Shape: Ovate. Apex: Cuspidate. Margin: Entire. Texture, upper surface: Smooth, glabrous. Texture, lower surface: Slightly pubescent. Color, upper surface: Close to 146B. Color, lower surface: Close to 146B to 146C.

*Bracts.*—Quantity/arrangement: About ten in a single whorl. Length: About 2.3 cm. Width: About 5 mm. Shape: Lanceolate. Apex: Sharply acute. Margin: Entire. Texture, upper and lower surfaces: Pubescent. Color, upper and lower surfaces: Close to 146B.

*Peduncles.*—Length: About 4.2 cm. Diameter: About 2 mm. Angle: Straight to slightly bent. Strength: Strong, flexible. Texture: Pubescent. Color: Close to 144A.

*Reproductive organs.*—Androecium: Stamen quantity per flower: Numerous, about 100. Anther shape: Reniform. Anther size: About 2 mm by 1.5 mm. Anther color: Close to 4B to 4C. Amount of pollen: None observed. Gynoecium: Pistil quantity per flower: One with five stigmas. Pistil length: About 3 cm. Style length: About 2.6 cm. Style color: Close to 155D; towards the apex, overlain with 57A. Stigma shape: Rounded. Stigma color: Close to 62B to 62C. Ovary color: Close to 154C.

*Seed/fruit.*—Seed and fruit production has not been observed.

Garden performance: Plants of the new *Hibiscus* have been observed to be tolerant to wind and rain and to have excellent garden performance.

Hardiness: Plants of the new *Hibiscus* have been observed to be hardy to USDA Zone 5.

High temperature tolerance: Plants of the new *Hibiscus* have been observed to tolerate temperatures of about 40° C.

Disease/pest resistance: Plants of the new *Hibiscus* have not been observed to be resistant to pathogens and pests common to *Hibiscus*.

It is claimed:

1. A new and distinct *Hibiscus* plant named 'Carafe Yobordeaux', as illustrated and described.

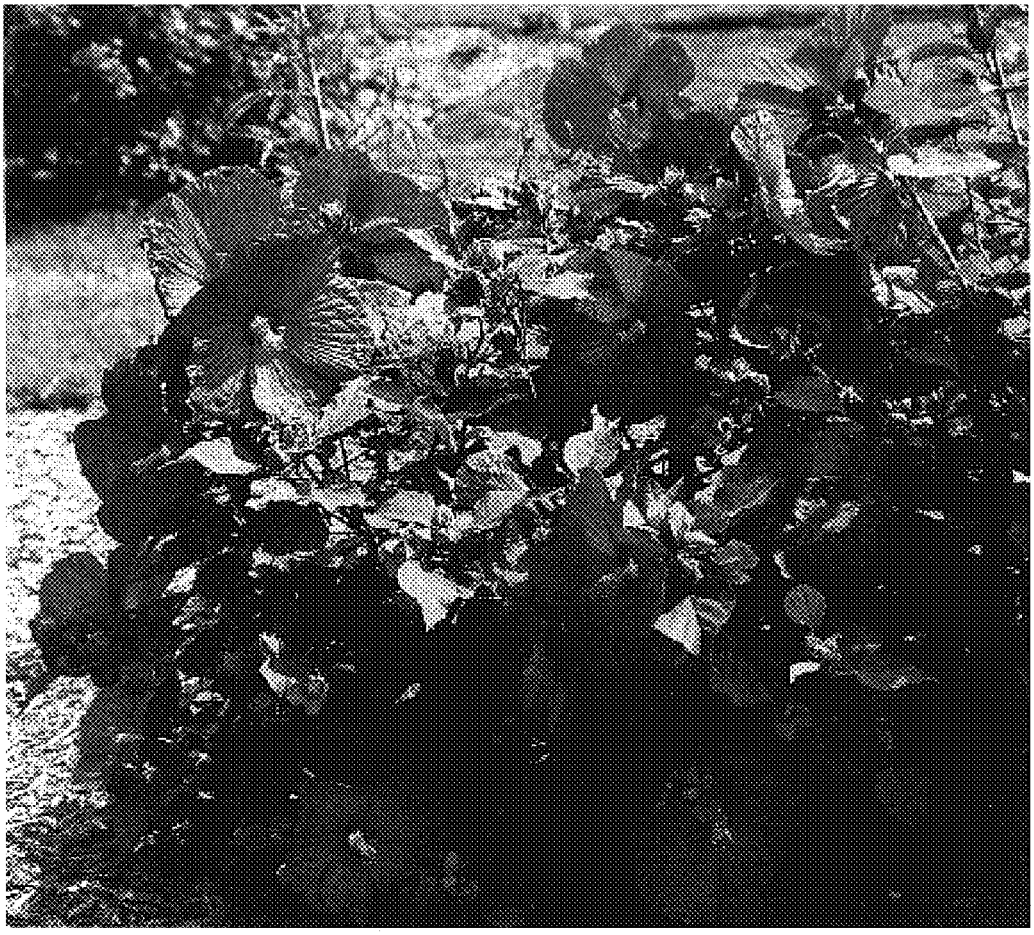

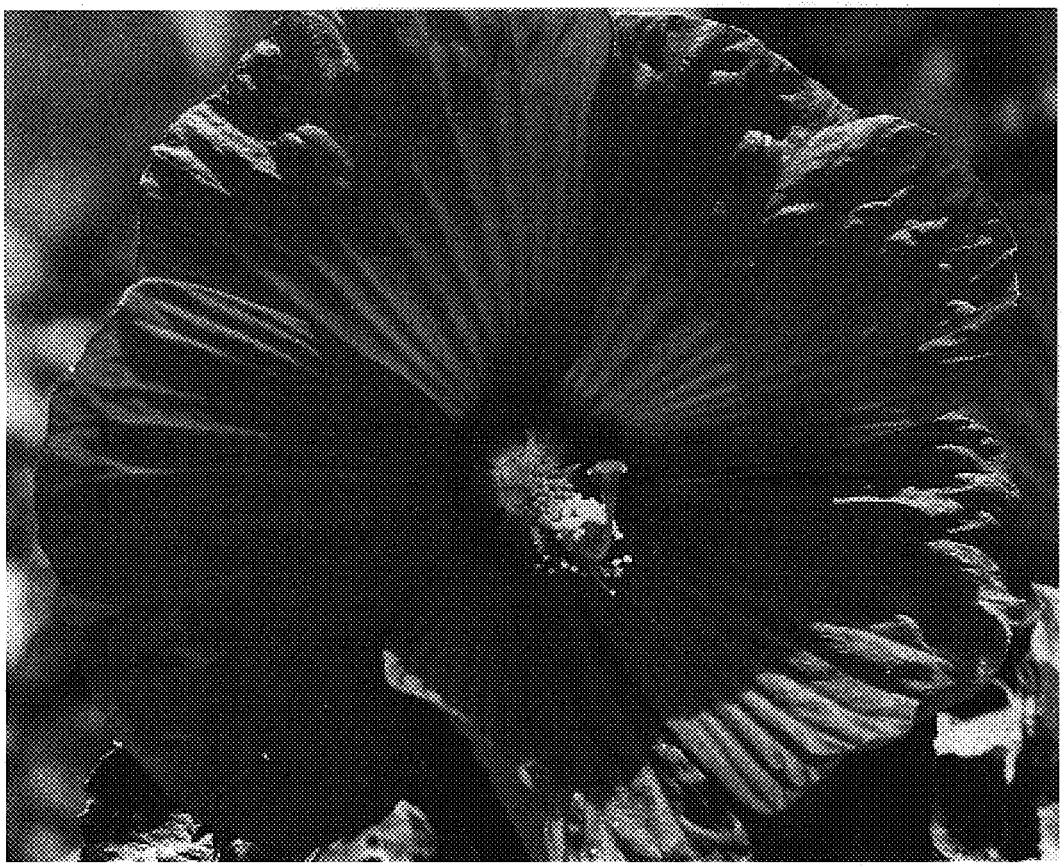

* * * * *